United States Patent [19]
Choisser

[11] Patent Number: 4,795,343
[45] Date of Patent: Jan. 3, 1989

[54] DISPOSABLE ROTARY TOOL ASSEMBLY FOR CLEANING TEETH

[76] Inventor: George P. Choisser, 14130 Michael, Orland Park, Ill. 60462

[21] Appl. No.: 97,906

[22] Filed: Sep. 17, 1987

[51] Int. Cl.$^4$ .................................................. A61C 1/16
[52] U.S. Cl. ...................................... 433/116; 433/132
[58] Field of Search ................ 433/116, 125, 166, 132

[56] References Cited

U.S. PATENT DOCUMENTS

| | | | |
|---|---|---|---|
| 3,955,284 | 5/1976 | Balson | 433/132 |
| 4,248,589 | 2/1981 | Lewis | 433/80 |
| 4,259,071 | 3/1981 | Warden et al. | 433/166 |
| 4,693,871 | 9/1987 | Geller | 433/116 |

*Primary Examiner*—Robert Peshock
*Attorney, Agent, or Firm*—Ernest Kettelson

[57] ABSTRACT

A disposable rotary tool assembly for cleaning teeth comprising what is known in the dental profession as a prophylactic angle, a small cup-like member made of rubber or similar material having a frusto-conical shape which is placed against a patient's teeth and rotated for cleaning and polishing, and a disposable operating assembly for rotating the same which is connected to a dentist's air syringe and powered by pressurized air instead of being connected to the dentist's hand piece as at present which requires a relatively expensive shaft driven connector, not practical to dispose of after each use with a single patient. The disposable operating assembly in accordance with this invention comprises a flexible sheet sheath of plastic such as polyethylene in which the elongated nozzle and body of the air syringe is inserted, a turbine chamber also of plastic material connected at the end of the sheath which is press fitted or otherwise mounted on the outlet tip of the air syringe nozzle, having a small plastic or hard rubber turbine within for rotation by a flow of pressurized air from the air syringe, to in turn rotate the small prophylactic angle piece connected thereto. The entire operating assembly is removed from the air syringe and can be disposed of after use with a single patient in view of the inexpensive nature of the materials used.

20 Claims, 4 Drawing Sheets

DISPOSABLE ROTARY TOOL ASSEMBLY FOR CLEANING TEETH

BACKGROUND OF THE INVENTION

This invention relates to the field of tools and devices for cleaning and polishing teeth used by members of the medical and dental professions. It is directed particularly to those cleaning and polishing devices which are rotated or reciprocated by a power source and require a drive mechanism for their operation.

A commonly used cleaning and polishing device of this kind is known in the dental profession as a prophylactic angle, a small cup-like device of rubber or similar material having a circular cross-section so it is rotatable and having a frusto-conical shape in elevation providing an angled or diagonally extending annular surface for better reaching recessed portions of the patient's row of teeth.

The present and prior art practice is to use the dentist's hand piece to drive and rotate the prophylactic angle. The dentist's hand piece is a powered tool to which a number of tools and devices can be connected such as drills, and the like. It is an expensive tool, one that wears out with constant use and has to be regularly replaced. When this tool is used to drive the prophylactic angle, an adapter or shaft driven connector has to be employed, which is also an expensive item and cannot be disposed of after use with a single patient. The prophylactic angle is secured to the adaptor or connector as presently used and the same one is therefore used over and over again for successive numbers of patients.

It would be desirable for sanitary purposes to have a throw-away mechanism for driving the prophylactic angle cleaning and polishing member so it could be disposed of after use with each individual patient and a completely new one used for each successive patient. It would also be desirable to use a different power source which is less expensive than the presently used hand piece and does not wear out as rapidly.

The present invention accomplishes both of those goals. It comprises an elongated flexible sheet sheath of plastic such as polyethylene which can be slipped on and over the elongated nozzle and head of the dentist's air syringe tool connected to and powered by a source of pressurized air. A plastic fitting at one end of the sheath is secured to the outlet end of the air syringe nozzle, such plastic fitting having a small turbine chamber and turbine mounted therein, also made of inexpensive disposable material, for rotation of the turbine when pressurized air is flowed through the air syringe nozzle into the turbine chamber. The prophylactic angle member is connected to the turbine and rotates with the turbine.

At the opposite end of the elongated flexible sheath is a coupling structure for securing the device to the head of the air syringe. The coupling structure is in the form of a hood which fits over the air syringe head, but with a slot along the rear wall portion to receive the stem of the palm buttom valve operator, projecting from the upper rear wall of the air syringe head, as the hood portion is placed over the head. Thus, when the disposable operating mechanism in accordance with the present invention is put in place on the air syringe, the dentist can control operation of the rotary prophylactic angle member by the palm of his hand, pushing the palm button in to open the valve and admit pressurized air to rotate the prophylactic angle member and letting up on the palm button which is normally biased outwardly to the valve closed position when he wants to stop rotation of the device. This is a further advantage of using the air syringe tool to power the prophylactic angle, since when using the hand piece as the power source the dentist has to control its "off-on" operation by a foot pedal which is less responsive and somewhat harder, somewhat more awkward to do.

The air syringe tool is less expensive than the hand piece, has less moving parts to wear, and enables the dentist's more expensive hand piece to last longer when a different power tool can be used for the cleaning and polishing function performed by the rotary prophylactic angle member.

After a patient's teeth have been cleaned and polished by the prophylactic angle driven by the dentist's air syringe and the disposable operating mechanism in accordance with this invention, the device can be easily slipped off of the air syringe and thrown away after use with a single patient. A new previously unused prophylactic angle and disposable operating mechanism in accordance with this invention can be used for each successive patient.

SUMMARY OF THE INVENTION

It is an object of the invention to provide a disposable rotary tool assembly for cleaning and polishing teeth which for sanitary reasons can be disposed of after use with a single patient, and a new, previously unused one used for each successive patient.

It is an object of the invention to provide a disposable rotary tool assembly for cleaning and polishing teeth which can be used with and powered by the dentist's air syringe tool to save wear and tear on his hand piece tool.

It is an object of the invention to provide a disposable rotary tool assembly for cleaning and polishing teeth which comprises an operating mechanism made entirely of non-metallic materials, including a non-metallic turbine and turbine chamber for connection to a source of pressurized air to operate and rotate the turbine.

DESCRIPTION OF THE PREFERRED EMBODIMENT

Figure 1:
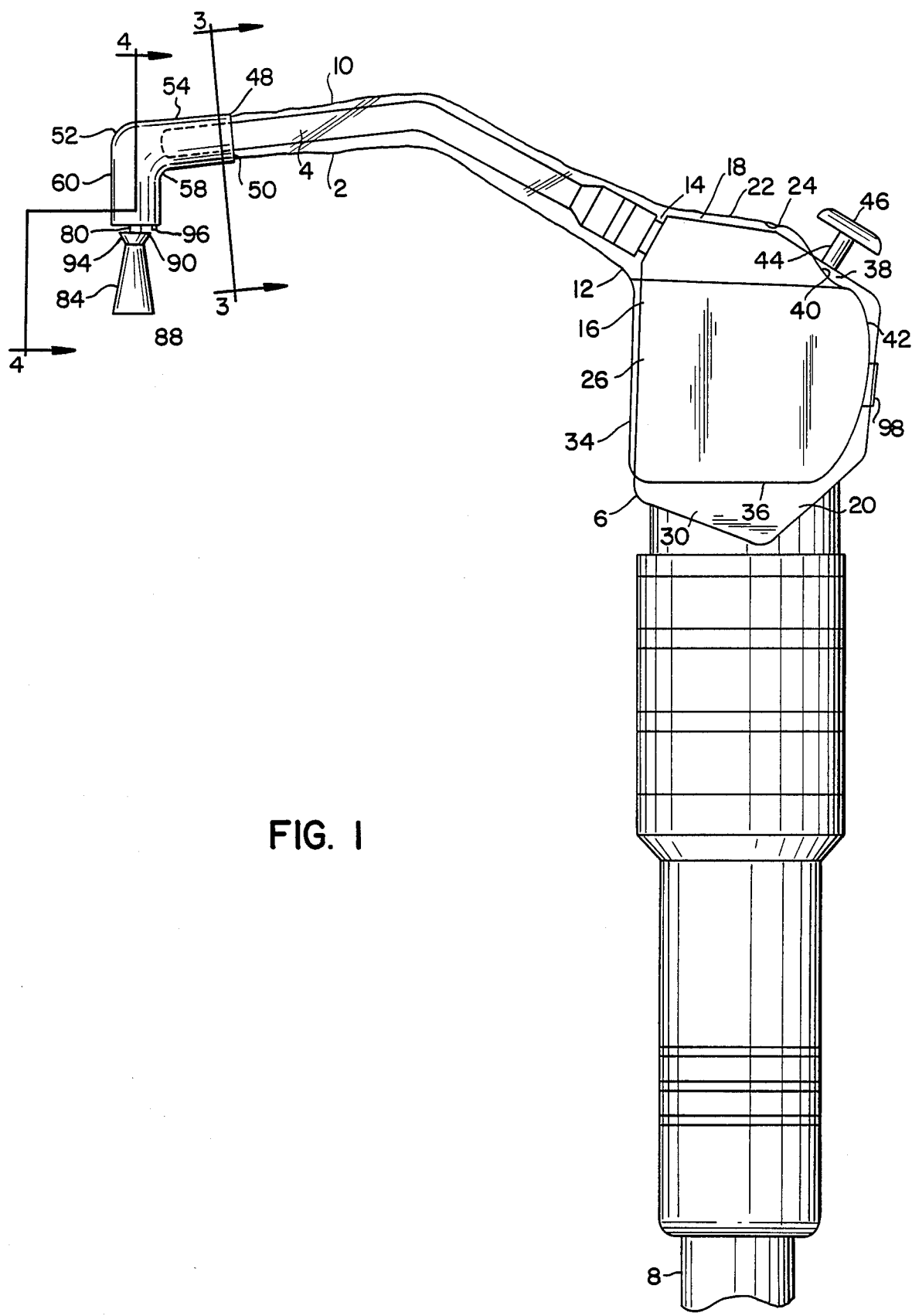
FIG. 1 is a side elevation view of a dentist's air syringe tool having a disposable rotary tool assembly for cleaning and polishing teeth in accordance with this invention connected thereto.
Figure 2:
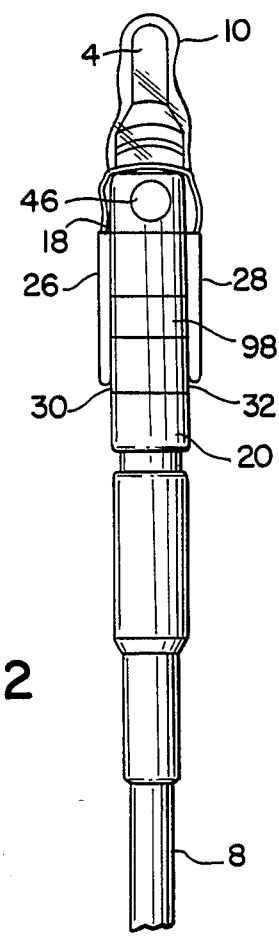
FIG. 2 is an elevation view from the rear of the air syringe tool and disposable rotary tool assembly shown in FIG. 1.
Figure 3:
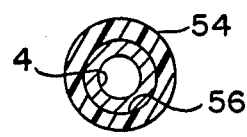
FIG. 3 is a section view taken on line 3—3 of FIG. 1.
Figure 4:
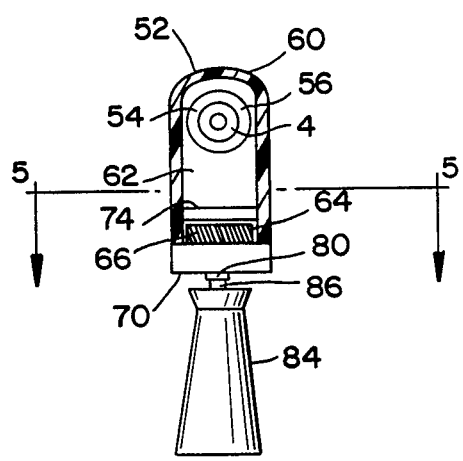
FIG. 4 is a section view taken on line 4—4 of FIG. 1.
Figure 5:
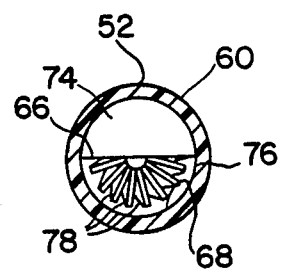
FIG. 5 is a section view taken on line 5—5 of FIG. 4.
Figure 6:
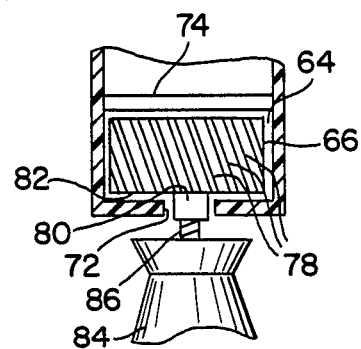
FIG. 6 is an elevation view of the turbine used in the rotary tool assembly of this invention taken from the front and showing it in place in the turbine chamber with the front wall portion broken away.
Figure 7:
FIG. 7 is a bottom plan view of the turbine shown in FIG. 6.
Figure 8:
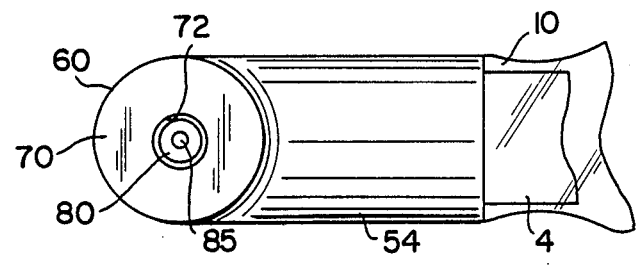
FIG. 8 is a bottom plan view of the operating assembly end of the present invention with the rotary tooth cleaning member or prophylactic angle removed.

A disposable rotary tool assembly for cleaning and polishing teeth in accordance with this invention includes an elongated flexible sheath 2 of flexible sheet material such as polyethylene or the like receivable over the elongated nozzle 4 of an air syringe 6 commonly used by dentists for flushing out material between their patient's teeth by directing a stream of compressed air thereon. The air syringe 6 is connected to a source of compressed air by the flexible air hose 8.

The flexible sheet 2 includes an elongated tubular portion 10 terminating at one end 12 in an opening 14 to a coupling structure 16 having a cavity 18 to receive the head 20 of an air syringe 6. The coupling structure 16 includes a top wall 22 corresponding in shape and dimension to the top wall 24 of the air syringe 6, a pair of side walls 26 and 28 spaced apart a distance corresponding to the distance the respective side walls 30 and 32 of the air syringe 6 are spaced apart whereby the coupling chamber side walls 26 and 28 snugly receive and bear against respective air syringe side walls 30 and 32, and a front wall 34 integrally joined to and extending between the coupling chamber side walls 26 and 28. The bottom wall 36 of the coupling structure 16 is open to receive the upper portion of the air syringe body 38 therein. A slot 40 extends downwardly along the rear wall 42 of the coupling structure 16, opening to the open bottom wall 36, to receive the stem 44 of the palm button valve operator 46 of the air syringe as the coupling chamber 16 is placed over the air syringe body 38 and fitted thereon.

The elongated tubular portion 10 of the flexible sheath 2 terminates at the opposite end 48 in an opening 50 to an operating assembly 52.

The operating assembly 52 includes an elongated tubular neck 54 having a central bore 56 extending therethrough with an internal diameter corresponding in size to the external diameter of the elongated nozzle 4 of the air syringe 6 for a press fit of the nozzle 4 within the bore 56 of the elongated tubular neck 54. The elongated neck 54 terminates at its forward or downstream end 58 in an integrally formed power head 60, comprising a pressurized air chamber 62 opening to the central bore 56 of elongated neck 54 at one end and having a turbine cylinder 64 formed in the other end. A small turbine 66 is seated for rotation in the turbine cylinder 64 bounded by a cylindrical side wall 68, a bottom wall 70 having a central aperture 72 extending through the bottom wall 70, and a top wall 74 having a cut-away portion 76 in the shape of a semi-circle for passage of compressed air from the nozzle 4 of the air syringe 6 through the elongated tubular neck 54 of the operating assembly 52, into the compressed air chamber 62 thereof, and then through the cut-away portion 76 into the turbine cylinder 64 to contact the vanes 78 of the turbine cylinder 66 causing it to rotate.

The turbine 66 includes a short drive shaft 80 extending from its lower surface 82 through the central aperture 72 for connection of a rotary tooth cleaning member 84. The drive shaft 80 has an integrally threaded bore 85 to receive the externally threaded connecting shaft 86 of the rotary cleaning member 84. The rotary cleaning member 84 is made of a resilient material such as rubber, is circular in cross-section and substantially frusto-conical configuration in side elevation, having a larger diameter at its outer free end 88, narrowing toward a smaller diameter toward its connected end 90, flaring back outwardly toward a larger diameter at its inward connected end 90 to form a short outwardly flared annular rim portion 94.

The elongated tubular portion 10 of the flexible sheath 2 is made of a flexible sheet material such as polyethylene. The coupling structure 16 may be of the same material, although the side walls 26 and 28 thereof may be reinforced with a less flexible, more rigid material such as vinyl or polycarbonate or a relatively rigid rubber material to enable the side walls to snugly grip and hold the respective side walls 30 and 32 of the air syringe 6. The operating assembly 52 is preferably made of a more rigid plastic or rubber material for shape retention of the pressurized air chamber 62 and turbine cylinder 64 when pressurized air is flowed therein, and the elongated tubular neck is preferably made of the same plastic or rubber material having more rigidity but yet enough resilience to expand for reception of the elongated nozzle 4 of the air syringe therein and to then frictionally grip and hold the nozzle 4 therein while pressurized air is flowed from the nozzle into the pressurized air chamber 62 and into the turbine cylinder 64 to rotate the turbine 66 and the rotary cleaning member 84. The coupling structure 16 and the operating assembly 52 may be joined to the elongated tubular portion 10 of the flexible sheath 2 by heat sealing, adhesives or other means, or the entire unit may be integrally formed as a single unitary structure of the same material as used for the operating assembly 52. The entire unit may be integrally formed as a unitary structure of the same more flexible sheet material as the elongated tubular portion, with reinforcing material applied to the parts of the operating assembly 52 and of the side wall portions of the coupling structure 16 for gripping retention of corresponding parts of the air syringe 6.

The small turbine 66 may be made of a rigid plastic material such as vinyl, or hard rubber.

To use the device, the nozzle 4 of an air syringe 6 is entered into and through the elongated tubular portion 10 of the sheath 2, for gripping reception into the elongated tubular neck 54 of the operating assembly 52 for passage of pressurized air through the nozzle 4 into the pressurized air chamber 62 of the operating assembly 52, through the cut-away portion 76 of the top wall 74 of the turbine cyclinder 64, to contact the vanes 78 of the turbine 66 causing it to rotate, freely floating within the turbine cylinder 64, and rotating the rotary cleaning member 84 connected thereto. When the nozzle 4 of the air syringe 6 is fully seated within the elongated tubular neck 54 of the sheath 2, the body 38 of the air syringe is in position for reception into the coupling structure 16 through its open bottom wall 36. When fully received and seated therein, the side walls 26 and 28 of the coupling chamber 16 grip the respective side walls 30 and 32 of the air syringe 6 to hold the coupling chamber 16 securely in place. The stem 44 of the palm button valve operator 46 of the air syringe 6 is received in the slot 40 along the rear wall 42 of the coupling chamber 16, with the palm button valve operator 46 projecting outwardly for operation by the dentist to cause pressurized air to flow into and through the air syringe 6 and operating assembly 52 of the sheath 2 for operation of the rotary cleaning member 84 as described.

The rotary cleaning member 84 is known in the dental profession as a prophylactic angle. It is usually connected to an operating assembly, which in turn connects to a conventional hand piece having a rotary drive mechanism, such hand piece used for multiple purposes such as to operate drills, polishing tools and the like. A foot pedal is typically used to control operation of the hand piece, whereas an air syringe 6 used to power and operate the rotary cleaning member 84, or prophylactic angle in accordance with the prsent invention can be controlled with the palm of dentist's hand which holds and directs the application of the rotary cleaning member 84, or prophylactic angle, to the patient's teeth. Thus, simply by pressing against the palm button valve operator 46, pressurized air can be applied to rotate the member 84, and by letting up on such valve operator 46, which is normally biased outwardly to the valve closed position, the flow of pressurized air can be stopped to discontinue rotary movement of the member 84.

The syringe tool 6, can, as an alternative, be connected to a source of pressurized water, which can be flowed through the device in the same manner as described above to cause the turbine 66 and rotary cleaning member 84 to rotate. The bottom wall 70 of the turbine cylinder 64 includes a discharge port 96 for venting the turbine cylinder 64.

If desired, a stretchable band 98 may be connected between the rear edges of the side walls 26 and 28 of the coupling structure to aid in holding them snugly against the respective side walls 30 and 32 of the air syringe head 20.

The disposable rotary tool in accordance with this invention may be disposed of in its entirety after use with a single patient. The materials used in making the deivce, and it's simplicity of construction, make it inexpensive to make thereby making it feasible to discard after using with a single patient. Use of the air syringe 6 as the operating power source rather than the hand piece which is presently used, also saves wear and tear of the relatively more expensive hand piece as well as the air syringe being easier to control and operate than when the hand piece is used as the operating power source.

All of the materials used to make the disposable rotary tool assembly in accordance with this invention may be non-metallic except for the small connecting shaft 86 of the rotary cleaning member or prophylactic angle 84 which is typically of metal. All of such materials and parts are inexpensive, making it feasible to dispose of the entire assembly after use with a single patient. The coupling structure 16, elongated flexible sheath 10 and entire operating assembly 52 with the prophylactic angle 84 still connected can be easily uncoupled and removed from the air syringe 6 and then thrown away. A completely new disposable rotary tool assembly and new prophylactic angle 84 connected thereto can be easily slipped on the air syringe 6 for the next patient on which such prophylactic angle is to be used.

I claim:

1. A rotary tool for cleaning teeth, comprising a portable disposable structure to support a turbine therein for rotation, said rotary tool being a single patient tool for personal use on a single individual patient and disposable upon completion of use on such single individual patient, a turbine rotatably mounted therein, positioning means to position said turbine for operating contact by a source of pressurized air, a rotary tooth cleaning tool connected to rotate with said turbine when so contacted by said soruce of pressurized air, said portable disposable structure including elongated disposable protective means having an elongated passageway joined at one end to said positioning means and open at its other end to receive a pressurized air dispensing tool in position to direct said source of pressurized air into operating contact with said turbine and to protect said dispensing tool while received therein from contact by external substances.

2. A rotary tool for cleaning tool as set forth in claim 1, wherein said positioning means to position said turbine for operating contact by a source of pressurized air includes a tubular member for connection to flow pressurized air from said pressurized air source to said turbine, detachable means to detachably connect and secure said tubular member in place to flow said pressurized air to said turbine, said positioning means including said detachable means, said portable disposable structure includes a turbine chamber, said turbine being rotatably mounted in said turbine chamber, said tubular member being positioned to direct said pressurized air to said turbine chamber for rotation of said turbine, and holding means to hold said tubular member in place to flow said pressurized air to said turbine chamber.

3. A rotary tool for cleaning teeth as set forth in claim 2, wherein said detachable means to detachably connect and secure said tubular member in place to flow said pressurized air from said pressurized air source to said turbine includes an elongated cylindrical nozzle having an external diameter of a given dimension positioned to receive pressurized air from said pressurized air source, said tubular member having an internal diameter corresponding to said external diameter of said elongated nozzle, said tubular member being sufficiently resilient and elastic for expansion of its said internal diameter enough to receive said elongated nozzle therein and to thereupon bear tightly against the cylindrical surface of the portion of said nozzle received therein in order to securely hold said tubular member to said nozzle.

4. A rotary tool for cleaning teeth as set forth in claim 2, wherein said holding means to hold said tubular member in place to flow said pressurized air to said turbine chamber includes an operating assembly housing, said operating assembly housing being included in said portable disposable structure at a first end portion thereof, said housing being connected to said tubular member, said housing including a pressurized air chamber opening to said tubular member to receive pressurized air therein from said pressurized air source, said turbine chamber opening to said pressurized air chamber of said housing to receive a flow of pressurized air therefrom for rotation of said turbine.

5. A rotary tool for cleaning teeth as set forth in claim 4, wherein said turbine comprises a rotary member having a central axis and a plurality of vanes extending radially outwardly from said central axis, said turbine including an upstream side facing upstream toward said source of pressurized air and a downstream side facing downstream away from said source of pressurized air, a drive shaft extending from said downstream side of said turbine in line with said central axis of said turbine and projecting outwardly of said turbine chamber for connection of said rotary tooth cleaning tool thereto for rotation of said rotary tooth cleaning tool when said turbine is rotated by said flow of pressurized air into said turbine chamber, said turbine being free floating within said turbine chamber, said turbine chamber including an upstream retaining wall portion facing said upstream side of said turbine to retain said turbine in said turbine chamber, said upstream retaining wall portion being spaced apart from said upstream side of said turbine a sufficient distance to permit it to rotate freely within said turbine chamber, said upstream retaining wall portion including an opening for flow of pressurized air from said pressurized air source into said turbine chamber, said turbine chamber including an annular retaining wall facing the annular periphery of said turbine to retain said turbine centered within said turbine chamber as it rotates, said annular retaining wall being spaced apart from said annular periphery of said turbine a sufficient distance to permit it to rotate freely within said turbine chamber, said entire operating assembly housing and said turbine being of inexpensive, non-metallic material and disposable after use with a single patient.

6. A rotary tool for cleaning teeth as set forth in claim 1, wherein said portable disposable structure is elongated and includes a first end and an oppositely disposed second end, an operating assembly housing at said first end, said turbine being rotatably mounted in said operating assembly housing, a coupling structure at said second end of said elongated portable disposable structure, said coupling structure including first and second side walls which may be spaced apart a predetermined limited distance for gripping engagement of the body of a pressurized air supply tool therebetween, including said pressurized air supply tool, said pressurized air supply tool comprising said body, an elongated nozzle extending from said body, said portable disposable structure being mountable on said pressurized air supply tool, said elongated nozzle of said air supply tool being received in said elongated passageway of said disposable protective means of said portable disposable structure when said structure is mounted on said tool, said positioning means of said portable disposable structure being connected to said nozzle of said pressurized air supply tool to direct pressurized air to said turbine for rotation thereof when said portable disposable structure is mounted on said air supply tool.

7. A rotary tool for cleaning teeth as set forth in claim 6, wherein said operating assembly housing, said turbine, said coupling structure, said elongated disposable protective means having said elongated passageway, and said rotary tooth cleaning tool being of inexpensive, disposable materials, said entire portable, disposable structure comprising said housing, turbine, coupling structure, elongated protective means, and rotary tooth cleaning tool being removable from said air supply tool and disposable after use with a single patient.

8. A rotary tool for cleaning teeth, comprising a portable structure to support a turbine therein for rotation, a turbine rotatably mounted therein, a portable hand tool connectible to a source of pressurized fluid having a discharge nozzle for discharge of pressurized fluid therefrom, said portable structure including elongated disposable protective means having an elongated passageway to receive said portable hand tool and discharge nozzle therein, said portable structure being removably mounted on said portable hand tool, and turbine positioning means to position said turbine rotatably mounted within said portable structure in proximity to said discharge nozzle for operating contact by pressurized fluid discharged from said nozzle, and a rotary tooth cleaning member to rotate with said turbine when so contacted by said source of pressurized fluid.

9. A rotary tool for cleaning teeth as set forth in claim 8, wherein said turbine positioning means includes a turbine chamber to position and retain said turbine within said turbine chamber for rotation therein, and nozzle connecting conduit means for connection to said discharge nozzle to flow pressurized fluid from said discharge nozzle to operate said turbine.

10. A rotary tool for cleaning teeth as set forth in claim 9, wherein said nozzle connecting conduit means includes an elongated tubular member, said discharge nozzle includes an elongated tubular discharge end portion, said elongated tubular discharge end portion of said discharge nozzle having an external diameter corresponding to the internal diameter of said elongated tubular member of said nozzle connecting conduit means for press fit reception and holding of said elongated tubular discharge end portion of said nozzle in said elongated tubular member of said nozzle connecting conduit means.

11. A rotary tool for cleaning teeth as set forth in claim 10, said portable structure including a pressure chamber between said nozzle connecting conduit means and said turbine chamber, said pressure chamber opening to said discharge nozzle to receive a volume of pressurized fluid therein from said discharge nozzle, said turbine chamber opening to said pressure chamber to receive a flow of pressurized fluid therein from said pressure chamber to rotate said turbine.

12. A rotary tool for cleaning teeth as set forth in claim 9, wherein said turbine is free floating within said turbine chamber, said turbine chamber including an annular retaining wall having a circumference sufficiently greater than the circumference of said turbine to permit it to rotate freely, an upstream retaining wall and a spaced apart downstream retaining wall extending laterally from said annular retaining wall and radially inwardly therefrom, said upstream and downstream retaining wall being spaced apart a sufficiently greater distance than the corresponding dimension of said turbine between said upstream and downstream retaining walls to permit it to rotate freely therebetween, said upstream retaining wall having an opening therein to receive a flow of pressurized fluid into said turbine chamber from said discharge nozzle of said portable hand tool.

13. A rotary tool for cleaning teeth as set forth in claim 12, wherein said turbine includes an upstream side facing said upstream retaining wall and a downstream side facing said downstream retaining wall, said downstream retaining wall having a circular aperture opening to the center of said turbine chamber, said turbine including a cylindrical drive shaft extending from said downstream side of said turbine in line with the central axis of said turbine and projecting through said circular aperture in said downstream retaining wall, said circular aperture having an internal diameter sufficiently greater than the external diameter of said cylindrical drive shaft of said turbine to permit said free floating turbine to rotate freely within said turbine chamber.

14. A rotary tool for cleaning teeth as set forth in claim 8, wherein said pressurized fluid is water.

15. A rotary tool for cleaning teeth as set forth in claim 8, wherein said pressurized fluid is air.

16. A rotary tool for cleaning teeth as set forth in claim 11, wherein said portable structure to support a turbine therein for rotation, including said turbine chamber, said nozzle connecting conduit means, said pressure chamber between said nozzle connecting conduit means and said turbine chamber, and said turbine are all made entirely of non-metallic material.

17. A rotary tool for cleaning teeth as set forth in claim 8, wherein said portable structure to support a turbine therein for rotation is elongated terminating at oppositely disposed first and second ends, an operating assembly housing at said first end for connection to said discharge nozzle of said portable hand tool for operation of said turbine, a coupling structure at said second end to couple said portable structure to support a turbine therein for rotation to a body portion of said portable hand tool, including said body portion of said portable hand tool, said discharge nozzle being elongated having a discharge end spaced apart from an input end, said body portion of said portable hand tool being spaced apart from said discharge end of said nozzle and connected to said input end thereof.

18. A rotary tool for cleaning teeth as set forth in claim 17, wherein said body portion of said portable hand tool includes spaced apart first and second side walls, said coupling structure of said portable structure to support a turbine therein for rotation having first and second spaced apart side walls to face and bear against respective ones of said first and second side walls of said body portion of said portable hand tool when coupled thereto, and including a rear wall having a facing portion to face and bear against a corresponding portion of the rear wall of said body portion of said portable hand tool, including said portion of the rear wall of said body portion of said portable hand tool.

19. A rotary tool for cleaning teeth as set forth in claim 17, wherein said portable hand tool is a dentist's air syringe, said air syringe including a valve and a push-button valve operator to operate said valve between a valve open and valve closed position, said valve being normally biased to the valve closed position at which time said push-button valve operator is in an extended position, said rear wall of said coupling structure including aperture means to receive said push-button valve operator therethrough.

20. A rotary tool for cleaning teeth as set forth in claim 17, wherein said facing portion of said rear wall of said coupling structure is an elastic strap having one connected to said first side wall of said coupling structure and its opposite end connected to said second side wall of said coupling structure.

* * * * *